US00PP35238P2

(12) United States Plant Patent
Koot

(10) Patent No.: US PP35,238 P2
(45) Date of Patent: Jun. 27, 2023

(54) ***BEGONIA* PLANT NAMED 'DOBEGICLALU'**

(50) Latin Name: *Begonia hybrida*
Varietal Denomination: Dobegiclalu

(71) Applicant: DUMMEN GROUP B.V., De Lier (NL)

(72) Inventor: Arjan Koot, Oeffelt (NL)

(73) Assignee: DUMMEN GROUP B.V., De Lier (NL)

( * ) Notice: Subject to any disclaimer, the term of this patent is extended or adjusted under 35 U.S.C. 154(b) by 0 days.

(21) Appl. No.: 18/081,679

(22) Filed: Dec. 14, 2022

(51) Int. Cl.
*A01H 5/02* (2018.01)
*A01H 6/18* (2018.01)

(52) U.S. Cl.
USPC ..... Plt./343
CPC ..... *A01H 6/185* (2018.05); *A01H 6/18* (2018.05)

(58) Field of Classification Search
USPC ..... Plt./343
CPC ..... A01H 5/02
See application file for complete search history.

*Primary Examiner* — Kent L Bell
(74) *Attorney, Agent, or Firm* — C. Anne Whealy

(57) ABSTRACT

A new and distinct cultivar of *Begonia* plant named 'Dobegiclalu', characterized by its relatively compact, semi-upright to outwardly spreading and mounded plant habit; moderately vigorous growth habit; freely basal branching habit; very dark brown-colored leaves; freely and continuously flowering habit; and large double-type flowers that are white in color.

1 Drawing Sheet

Botanical designation: *Begonia hybrida.*
Cultivar denomination: 'DOBEGICLALU'.

BACKGROUND OF THE INVENTION

The present invention relates to a new and distinct cultivar of *Begonia* plant, botanically known as *Begonia hybrida*, and hereinafter referred to by the name 'Dobegiclalu'.

The new *Begonia* plant is a product of a planned breeding program conducted by the Inventor in De Lier, The Netherlands. The objective of the breeding program was to develop new compact, freely branching and freely flowering *Begonia* plants with large and attractive flowers.

The new *Begonia* plant originated from a cross-pollination made by the Inventor during the autumn of 2016 of *Begonia hybrida* 'Dobegicposunris', disclosed in U.S. Plant Pat. No. 32,126, as the female, or seed, parent with *Begonia hybrida* 'I'CONIA First Kiss Hot Pink', not patented, as the male, or pollen, parent. The new *Begonia* plant was discovered and selected by the Inventor as a single flowering plant from within the progeny of the stated cross-pollination in a controlled greenhouse environment in De Lier, The Netherlands during the spring of 2017.

Asexual reproduction of the new *Begonia* plant by vegetative tip cuttings in a controlled greenhouse environment in De Lier, The Netherlands since the spring of 2017 has shown that the unique features of this new *Begonia* plant are stable and reproduced true to type in successive generations.

SUMMARY OF THE INVENTION

Plants of the new *Begonia* have not been observed under all possible combinations of environmental conditions and cultural practices. The phenotype may vary somewhat with variations in environment such as temperature and light intensity, without, however, any variance in genotype.

The following traits have been repeatedly observed and are determined to be the unique characteristics of 'Dobegiclalu'. These characteristics in combination distinguish 'Dobegiclalu' as a new and distinct *Begonia* plant:

1. Relatively compact, semi-upright to outwardly spreading and mounded plant habit.
2. Moderately vigorous growth habit.
3. Freely basal branching habit.
4. Very dark brown-colored leaves.
5. Freely and continuously flowering habit.
6. Large double-type flowers that are white in color.

Plants of the new *Begonia* can be compared to plants of the female parent, 'Dobegicposunris'. In side-by-side comparisons, plants of the new *Begonia* differ primarily from plants of 'Dobegicposunris' in the following characteristics:

1. Plants of the new *Begonia* are more freely branching than plants of 'Dobegicposunris'.
2. Leaves of plants of the new *Begonia* are dark brown in color whereas leaves of plants of 'Dobegicposunris' are dark greyed green in color.
3. Flowers of plants of the new *Begonia* are white in color whereas flowers of plants of 'Dobegicposunris' are dark yellow and orange red in color.

Plants of the new *Begonia* can be compared to plants of the male parent, 'I'CONIA First Kiss Hot Pink'. In side-by-side comparisons, plants of the new *Begonia* differ primarily from plants of 'I'CONIA First Kiss Hot Pink' in the following characteristics:

1. Leaves of plants of the new *Begonia* are dark brown in color whereas leaves of plants of 'I'CONIA First Kiss Hot Pink' are dark green in color.
2. Flowers of plants of the new *Begonia* are white in color whereas flowers of plants of 'I'CONIA First Kiss Hot Pink' are deep pink in color.

Plants of the new *Begonia* can be compared to plants of *Begonia hybrida* 'I'CONIA Bacio Peach', not patented. In side-by-side comparisons, plants of the new *Begonia* differ primarily from plants of 'I'CONIA Bacio Peach' in the following characteristics:

1. Plants of the new *Begonia* are broader than plants of 'I'CONIA Bacio Peach'.
2. Leaves of plants of the new *Begonia* are darker brown in color than leaves of plants of 'I'CONIA Bacio Peach'.
3. Plants of the new *Begonia* have larger flowers than plants of 'I'CONIA Bacio Peach'.
4. Flowers of plants of the new *Begonia* are white in color whereas flowers of plants of 'I'CONIA Bacio Peach' are soft yellow to peach in color.

BRIEF DESCRIPTION OF THE PHOTOGRAPH

The accompanying colored photograph illustrates the overall appearance of the new *Begonia* plant showing the colors as true as it is reasonably possible to obtain in colored reproductions of this type. Colors in the photograph may differ slightly from the color values cited in the detailed botanical description which accurately describe the colors of the new *Begonia* plant.

The photograph is a close-up view of a typical flowering plant of 'Dobegiclalu' grown in a container.

DETAILED BOTANICAL DESCRIPTION

Plants used for the aforementioned photograph and following observations and measurements were grown in 12-cm containers during the summer in a glass-covered greenhouse in De Lier, The Netherlands. During the production of the plants, day temperatures ranged from 20° C. to 35° C., night temperatures ranged from 17° C. to 25° C. and minium light level was 135 watt/$m^2$. Plants were twelve weeks old when the photograph and the description were taken. In the following description, color references are made to The Royal Horticultural Society Colour Chart, Fifth Edition, except where general terms of ordinary dictionary significance are used.

Botanical classification: *Begonia hybrida* 'Dobegiclalu'.

Parentage:

*Female, or seed, parent.*—*Begonia hybrida* 'Dobegicposunris', disclosed in U.S. Plant Pat. No. 32,126.

*Male, or pollen, parent.*—*Begonia hybrida* 'I'CONIA First Kiss Hot Pink', not patented.

Propagation:

*Type.*—By vegetative tip cuttings.

*Time to initiate roots, summer.*—About 18 days at temperatures about 22° C. to 30° C.

*Time to initiate roots, winter.*—About 21 days at temperatures about 20° C. to 22° C.

*Time to produce a rooted young plant, summer.*—About 22 to 25 days at temperatures about 22° C. to 30° C.

*Time to produce a rooted young plant, winter.*—About 25 to 28 days at temperatures about 20° C. to 22° C.

*Root description.*—Medium in thickness, fibrous; whitish grey in color, actual color of the roots is dependent on substrate composition, water quality, fertilizer type and formulation, substrate temperature and physiological age of roots; plants of the new *Begonia* have not been observed to form tubers.

*Rooting habit.*—Moderately freely branching; medium density.

Plant description:

*Plant form and growth habit.*—Semi-upright to outwardly spreading and mounded plant habit; relatively compact; freely basal branching with about three primary lateral branches each with about three secondary lateral branches; moderately vigorous growth habit and moderate growth rate.

*Plant height, soil level to top of foliar plane.*—About 19 cm.

*Plant height, soil level to top of floral plane.*—About 20 cm.

*Plant width.*—About 40 cm.

*Lateral branch description.*—Length: About 11 cm. Diameter: About 1 cm. Internode length: About 2 cm. Texture and luster: Pubescent; semi-glossy. Aspect: Upright to outwardly spreading. Strength: Moderately strong, flexible. Color, developing: Close to N144D; at the internodes, close to 144C. Color, developed: Close to 152B.

*Leaf description.*—Arrangement: Alternate, simple. Length: About 13.5 cm. Width: About 4.3 cm. Shape: Lanceolate. Apex: Narrowly acute. Base: Oblique. Margin: Senate; sinuses medium in depth and divergent. Texture and luster, upper and lower surfaces: Pubescent; semi-glossy. Venation pattern: Palmate; reticulate. Color: Developing leaves, upper surface: Close to 203D. Developing leaves, lower surface: Close to 187C. Fully expanded leaves, upper surface: Close to 203D; venation, close to 145A. Fully expanded leaves, lower surface: Close to 186A; venation, close to 145A. Petioles: Length: About 7 cm. Diameter: About 5 mm. Texture and luster, upper and lower surfaces: Smooth, glabrous; semi-glossy. Strength: Moderately strong; flexible. Color, upper surface: Close to 148B to 148C. Color, lower surface: Close to 148C.

Flower description:

*Flowering habit.*—Double-type flowers arranged in axillary cymes; freely flowering habit with typically about three flowers per inflorescence and about 53 open flowers and flower buds per plant at one time; flowers face upright to outwardly.

*Fragrance.*—None detected.

*Natural flowering season.*—Plants begin flowering about eight weeks after planting; long flowering period, in the garden plants flower freely and continuously from the late spring throughout the summer in Northern Europe and can be flowered year-round in greenhouses.

*Flower longevity.*—Individual flowers last about five weeks on the plant; flowers not persistent.

*Inflorescence height.*—About 6.5 cm.

*Inflorescence diameter.*—About 11 cm.

*Flower buds.*—Length: About 2.8 cm. Diameter: About 2.6 cm. Shape: Ovoid. Texture and luster: Smooth, glabrous; semi-glossy. Color: Close to 157C to 157D.

*Flower size.*—Diameter: About 7.2 cm by 7.4 cm. Depth (height): About 2 cm.

*Petals.*—Quantity per flower and arrangement: Typically four to five per flower arranged in a single whorl. Length: About 3.6 cm. Width: About 4.3 cm. Shape: Obovate. Apex: Rounded and emarginate. Base: Cuneate and truncate. Margin: Entire; not undulate. Texture and luster, upper surface: Smooth, glabrous; matte. Texture and luster, lower surface:

Smooth, glabrous; semi-glossy. Color: When opening, upper surface: Close to 157B. When opening, lower surface: Close to 157C. Fully opened, upper and lower surfaces: Close to NN155B; venation, close to NN155B; color becoming closer to NN155C with subsequent development.

*Petaloids.*—Quantity per flower and arrangement: Typically 32 per flower arranged in about six whorls. Length: About 3 cm. Width: About 1.6 cm. Shape: Obovate. Apex: Rounded. Base: Cuneate. Margin: Entire; slightly undulate. Texture and luster, upper and lower surfaces: Smooth, glabrous; semi-glossy. Color: When opening, upper surface: Close to 157B. When opening, lower surface: Close to 157C. Fully opened, upper and lower surfaces: Close to NN155B; venation, close to NN155B; color does not change with subsequent development.

*Sepals.*—Quantity per flower and arrangement: Typically two to five per flower arranged in a single whorl. Length: About 3.5 cm. Width: About 4 cm. Shape: Obovate. Apex: Rounded and emarginate. Base: Cuneate and truncate. Margin: Entire. Texture and luster, upper and lower surfaces: Smooth, glabrous; semi-glossy. Color: When opening, upper and lower surfaces: Close to 157B. Fully opened, upper and lower surfaces: Close to NN155B.

*Peduncles.*—Length: About 7 cm. Diameter: About 4 mm. Aspect: Semi-upright. Strength: Moderately strong; flexible. Texture and luster: Smooth, glabrous; glossy. Color: Close to 152C.

*Pedicels.*—Length: About 3 cm. Diameter: About 2 mm. Aspect: Upright to outwardly. Strength: Moderately strong; flexible. Texture and luster: Smooth, glabrous; glossy. Color: Close to 145A.

*Reproductive organs.*—Stamens: Quantity of stamens per flower: About three. Filament length: About 8 mm. Filament color: Close to 17A. Anther length: About 2 mm. Anther shape: Oval. Anther color: Close to N144C. Amount of pollen: Scarce. Pollen color: Close to 157A. Pistils: Quantity of pistils per flower: Three. Pistil length: About 7 mm. Style length: About 4.5 mm. Style color: Close to 15A. Stigma diameter: About 4 mm. Stigma shape: Curled, bi-lobed. Stigma color: Close to 17B. Ovary color: Close to 145B. Fruits and seeds: To date, fruit and seed development have not been observed on plants of the new *Begonia.*

Pathogen & pest resistance: To date, resistance to pathogens and pests common to *Begonia* plants has not been observed on plants of the new *Begonia.*

Temperature tolerance: Plants of the new *Begonia* have been observed to tolerate temperatures ranging from about 10° C. to about 35° C.

It is claimed:

1. A new and distinct *Begonia* plant named 'Dobegiclalu' as illustrated and described.

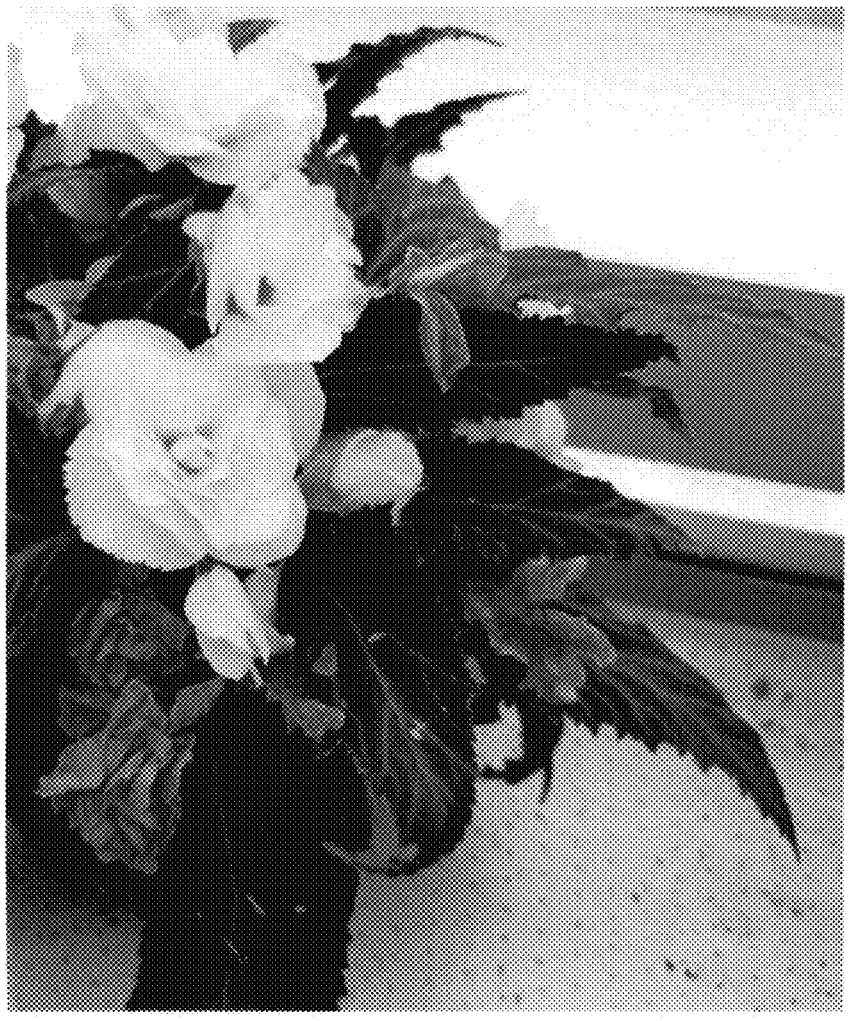

* * * * *